US010757303B2

(12) United States Patent
Kato

(10) Patent No.: US 10,757,303 B2
(45) Date of Patent: Aug. 25, 2020

(54) ENDOSCOPE APPARATUS

(71) Applicant: OLYMPUS CORPORATION, Tokyo (JP)

(72) Inventor: Takahiko Kato, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/394,019

(22) Filed: Apr. 25, 2019

(65) Prior Publication Data

US 2019/0335068 A1    Oct. 31, 2019

(30) Foreign Application Priority Data

Apr. 25, 2018  (JP) .................................. 2018-084409

(51) Int. Cl.
| | | |
|---|---|---|
| *A61B 1/04* | (2006.01) | |
| *H04N 5/225* | (2006.01) | |
| *G02B 23/24* | (2006.01) | |
| *A61B 1/00* | (2006.01) | |
| *A61B 1/07* | (2006.01) | |
| *A61B 1/05* | (2006.01) | |

(52) U.S. Cl.
CPC ......... *H04N 5/2253* (2013.01); *A61B 1/0011* (2013.01); *A61B 1/00114* (2013.01); *A61B 1/00117* (2013.01); *A61B 1/05* (2013.01); *A61B 1/07* (2013.01); *G02B 23/2484* (2013.01); *G02B 23/2492* (2013.01); *H04N 5/2254* (2013.01); *H04N 2005/2255* (2013.01)

(58) Field of Classification Search
CPC .................................................. H04N 5/2253
USPC ............................................................ 348/76
See application file for complete search history.

(56) References Cited

U.S. PATENT DOCUMENTS

| | | | | | |
|---|---|---|---|---|---|
| 5,685,823 | A | * | 11/1997 | Ito ..................... | A61B 1/00091 600/121 |
| 5,966,168 | A | * | 10/1999 | Miyazaki ........... | A61B 1/00096 348/68 |
| 6,142,932 | A | * | 11/2000 | Morizumi .......... | A61B 1/00091 348/47 |
| 6,796,939 | B1 | * | 9/2004 | Hirata ................ | A61B 1/00036 600/109 |
| 2005/0050707 | A1 | * | 3/2005 | Scott ........................ | B25B 9/02 29/426.5 |

(Continued)

FOREIGN PATENT DOCUMENTS

JP    2001-037713 A    2/2001

*Primary Examiner* — Leron Beck
(74) *Attorney, Agent, or Firm* — Scully, Scott, Murphy & Presser, P.C.

(57) ABSTRACT

An endoscope apparatus includes: an image pickup device; a glass lid that is provided on a distal end side ahead of a light receiving surface of the image pickup device and is fixed to a front face of the image pickup device in an integrated manner; and a frame body that covers at least a part of the image pickup device and the glass lid. The frame body includes a fixing region for fixing an image pickup circuit portion provided on a proximal end side opposite to the front face of the image pickup device, and a non-fixing region that keeps the distal end side relative to the light receiving surface of the image pickup device and the glass lid fixed to the light receiving surface of the image pickup device in a non-fixed state.

10 Claims, 9 Drawing Sheets

(56) References Cited

U.S. PATENT DOCUMENTS

| | | | | |
|---|---|---|---|---|
| 2009/0253955 | A1* | 10/2009 | Akiba | A61B 1/05 |
| | | | | 600/109 |
| 2016/0157705 | A1* | 6/2016 | Wataya | A61B 1/00087 |
| | | | | 600/104 |
| 2016/0266373 | A1* | 9/2016 | Sakai | G02B 23/2476 |
| 2016/0353976 | A1* | 12/2016 | Makiyama | G02B 23/2476 |
| 2017/0277498 | A1* | 9/2017 | Wood, Jr. | G06F 3/04886 |

* cited by examiner

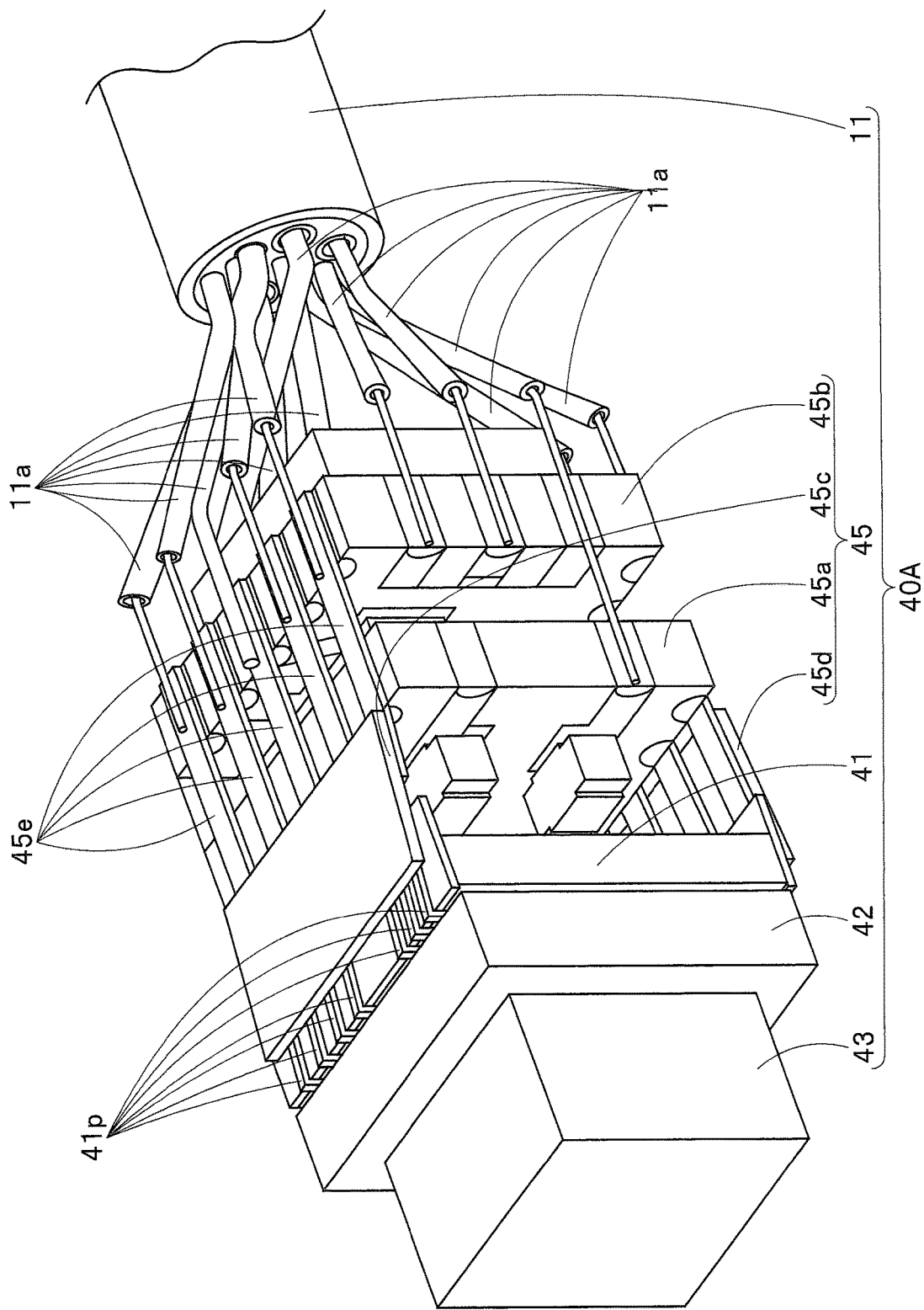

ENDOSCOPE APPARATUS

CROSS REFERENCE TO RELATED APPLICATION

This application claims the benefit of Japanese Application No. 2018-084409 filed in Japan on Apr. 25, 2018, the contents of which are incorporated herein by this reference.

BACKGROUND OF THE INVENTION

1. Field of the Invention

The present invention relates to an endoscope apparatus with a solid-state image pickup device incorporated in a distal end portion of an insertion portion.

2. Description of Related Art

Endoscope apparatuses have been used in the industrial field, the medical field, etc. The endoscope apparatuses each include a tubular insertion portion generally formed in an elongated shape. The insertion portion is inserted into, for example, a lumen that is an observation object. An image pickup apparatus including a solid-state image pickup device for obtaining an image of the observation object is incorporated in a distal end portion of the insertion portion.

An image signal obtained by performing image pickup and photoelectric conversion by means of the solid-state image pickup device is transmitted via an image pickup cable and formed into a video signal in a signal processing circuit. The video signal is outputted to a monitor apparatus, which is an external apparatus, and displayed on a screen of the monitor apparatus. An operator or a doctor observes an endoscopic image displayed on the screen.

The image pickup apparatus incorporated in the distal end portion includes the solid-state image pickup device with a glass cover bonded on the light receiving surface side, a circuit board and the image pickup cable and is covered by a shield member.

In other words, the solid-state image pickup device, the circuit board and a distal end-side part of the image pickup cable are disposed within an inner space of the shield member. Then, the solid-state image pickup device, the circuit board and signal wires are sealed by an adhesive charged inside the shield member.

In the industrial field, the insertion portion may be used for observation under high temperature, for example, observation of a boiler or a gas turbine engine. On the other hand, in the case of a medical endoscope, the insertion portion is inserted into a body from a trocar inserted or punctured in, e.g., a mouth cavity or an anus, or an abdomen. Then, after an end of an inspection or a treatment, the endoscopes are each exposed to a high temperature in autoclave sterilization.

Respective members and charged adhesives in each endoscope expand under high temperature. At the time of the expansion, stress may be imposed on the part of the bonding between the glass cover and the solid-state image pickup device, in a direction in which the glass cover and the solid-state image pickup device are detached from each other. Then, there is the problem of this stress causing the glass cover and the solid-state image pickup device to be detached from each other and thus causing occurrence of a defective image.

Japanese Patent Application Laid-Open Publication No. 2001-37713 indicates an electronic endoscope that prevents occurrence of a trouble such as detachment in, e.g., a bonding part, even if autoclave sterilization is repeatedly performed. In the electronic endoscope, a resin layer is provided to seal a solid-state image pickup device, a ceramic substrate and a core wire. An adhesive forming the resin layer is brought into a state in which the adhesive does not in any way adhere to or a part of the adhesive adheres to a shield frame, a cable fixing frame, an image pickup frame and a field lens disposed so as to cover the solid-state image pickup device, the ceramic substrate and the core wire, to relax stress and thus prevents the trouble of detachment due to expansion in high pressure and temperature vapor.

SUMMARY OF THE INVENTION

An endoscope apparatus according to an aspect of the present invention includes: an image pickup device; a device front-side optical member that is provided on a distal end side ahead of a light receiving surface of the image pickup device and is fixed to a front face of the image pickup device in an integrated manner; and a frame body that covers at least a part of the image pickup device and the device front-side optical member. The frame body includes a fixing region for fixing a device rear-side member provided on a proximal end side opposite to the front face of the image pickup device, and a non-fixing region that keeps the distal end side relative to the light receiving surface of the image pickup device and a device-side optical member of the device front-side optical member, the device-side optical member being fixed to the light receiving surface of the image pickup device, in a non-fixed state.

BRIEF DESCRIPTION OF THE DRAWINGS

FIG. 4A is a diagram illustrating a configuration of an image pickup section set;

DETAILED DESCRIPTION OF PREFERRED EMBODIMENTS

Figure 1:
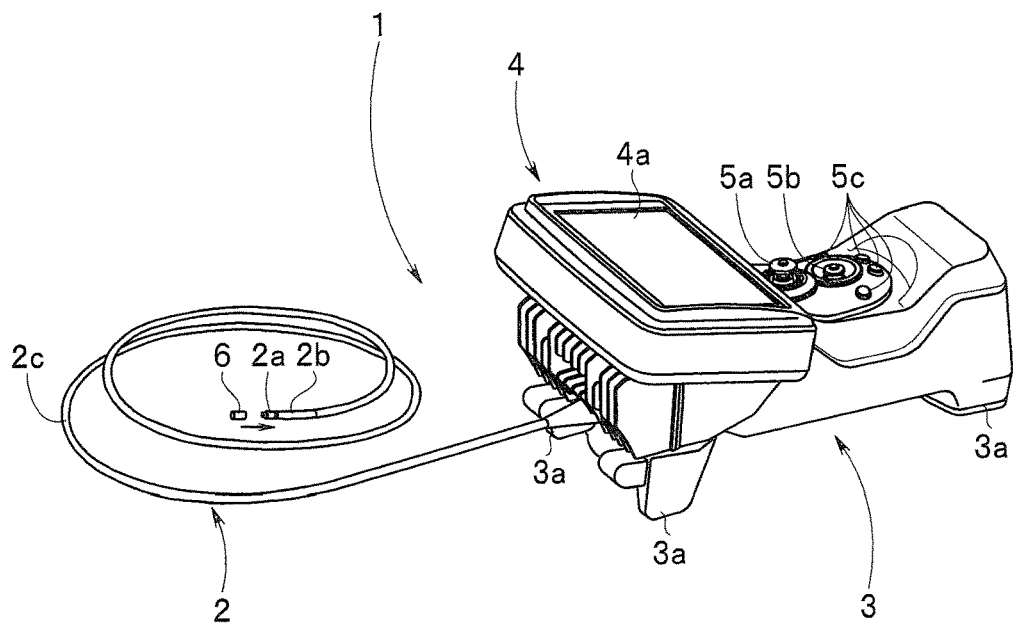
FIG. 1 is a diagram illustrating an example configuration of an endoscope apparatus to be used in the industrial field.

An embodiment of the present invention will be described below with reference to the drawings.

In each of the drawings used for the below description, in order to illustrate respective components in sizes that are large enough to be recognized in the drawing, the components may be illustrated in different scales. In other words, the present invention is not limited only to the illustrated forms in terms of, e.g., the number of the components, shapes of the components, ratios in size between the components and relative positional relationships between the respective components indicated in each drawing.

An endoscope apparatus 1, which is illustrated in FIG. 1, is used, for example, in the industrial field. The endoscope apparatus 1 includes an insertion portion 2 that can be inserted into an object, for example, a boiler or a gas turbine in a power generation plant.

The insertion portion 2 is flexible and has a tubular shape. The insertion portion 2 includes a distal end portion 2a, a bending portion 2b and a flexible tube portion 2c provided continuously in the mentioned order from the distal end side. The bending portion 2b includes, for example, a plurality of bending pieces provided consecutively and is actively bent in all directions around an insertion axis, the directions including upward, downward, leftward and rightward directions.

An apparatus body 3 is attached to the proximal end side of the insertion portion 2. The apparatus body 3 includes a light source unit (not illustrated) and is formed in, for example, a substantial rectangular parallelepiped shape. The apparatus body 3 has a function as a grasping portion and, e.g., a user can grasp the apparatus body 3 and performs observation.

Reference numeral 3a denotes a leg portion. Each leg portion 3a is provided so as to project from a lower face of the apparatus body 3. Observation without grasping the apparatus body 3 is enabled by placing the leg portions 3a on, e.g., a table.

Reference numeral 4 denotes a display section and includes a display surface 4a on which an endoscopic image, an operation menu, etc., are displayed. The display section 4 is, for example, a liquid-crystal panel (LCD) and may be provided with a touch panel.

A bending lever 5a, a pointing device 5b, a plurality of switches 5c, etc., are provided on the proximal end side relative to the display section 4. The bending lever 5a is used for operating the bending portion 2b to bend. The pointing device 5b is used for operating, e.g., a cursor displayed on the display surface 4a. Various functions and the like of the endoscope apparatus 1 are assigned to the plurality of switches 5c.

Note that the aforementioned upward, downward, leftward and right ward directions are conveniently defined so as to correspond to, for example, upward, downward, leftward and rightward directions in an endoscopic image picked up by an image pickup device and displayed on the display surface 4a. Reference numeral 6 denotes an optical adapter.

Figure 2:
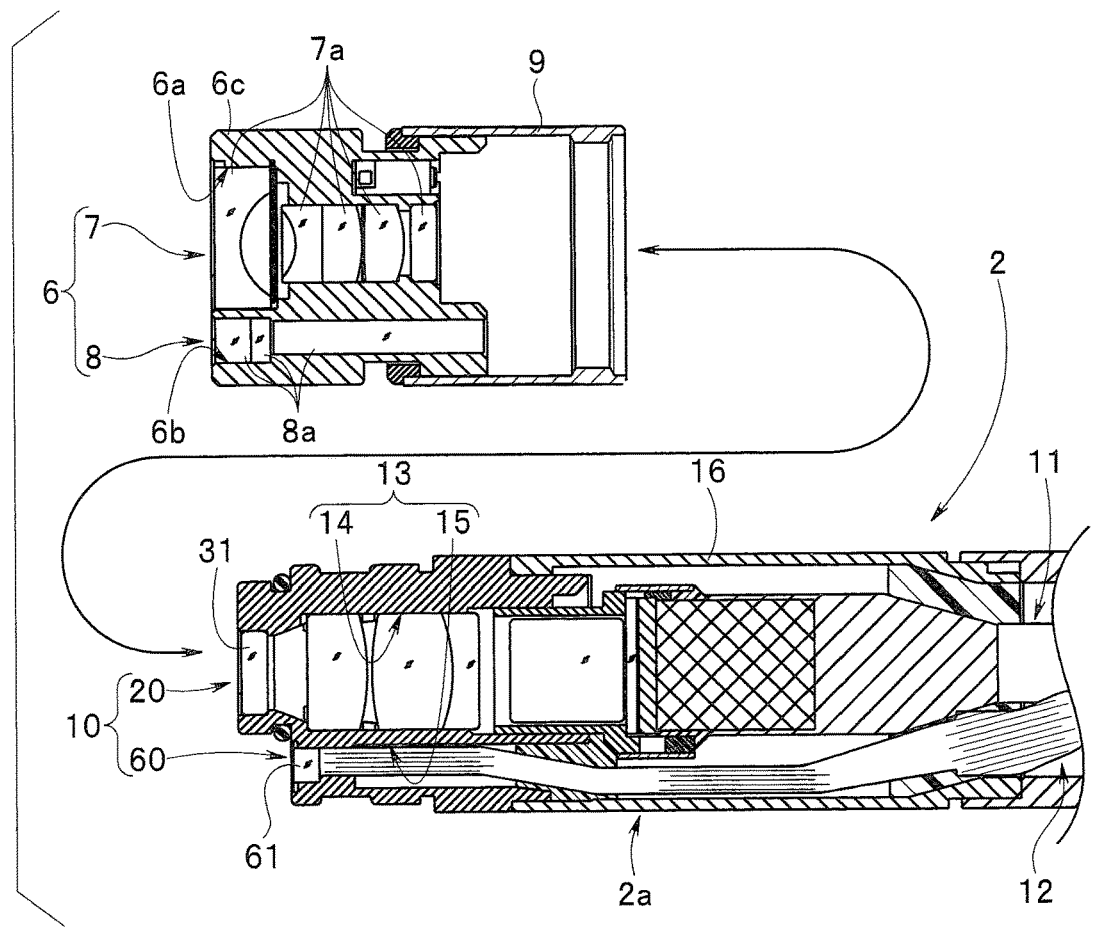
FIG. 2 is a diagram illustrating a relationship between an observation unit and an optical adapter in a distal end portion of an insertion portion.

As illustrated in FIG. 2, the optical adapter 6 is removably attachable to the distal end portion 2a of the insertion portion 2. The optical adapter 6 includes an observation optical system 7 and an illumination optical system 8. The observation optical system 7 is configured so as to observe ahead in an insertion direction. The illumination optical system 8 is configured so as to illuminate ahead in the insertion direction. In other words, the optical adapter 6 is of a front-view type.

An observation hole 6a and an illumination hole 6b are formed in a body member 6c of the optical adapter 6. An optical axis of the observation hole 6a and an optical axis of the illumination hole 6b are parallel to a longitudinal axis of the adapter.

The observation optical system 7 includes a plurality of optical lenses 7a and the optical lenses 7a are fixed inside the observation hole 6a. The illumination optical system 8 includes a plurality of relay lenses 8a and the relay lenses 8a are fixed inside the illumination hole 6b. Reference numeral 9 denotes a removable ring and is turnably attached to the body member 6c.

Note that the optical adapter 6 is not limited to a front-view type, but may be, e.g., a side-view type in which a side in an insertion direction is observed.

Reference numeral 10 in FIG. 2 denotes an observation unit, reference numeral 11 denotes an image pickup cable and reference numeral 12 denotes a light guide bundle. The image pickup cable 11 and the light guide bundle 12 extend toward the apparatus body 3.

The observation unit 10 is configured by an image pickup unit 20 and an illumination unit 60. Reference numeral 13 denotes a distal-end frame member formed of, for example, a stainless steel. An image pickup unit hole 14 and an illumination hole 15 are provided in the distal-end frame member 13. Reference numeral 31 denotes an observation lens and reference numeral 61 denotes an illumination lens.

A distal end face of the light guide bundle 12 is fixed to the illumination lens 31.

Figure 3:
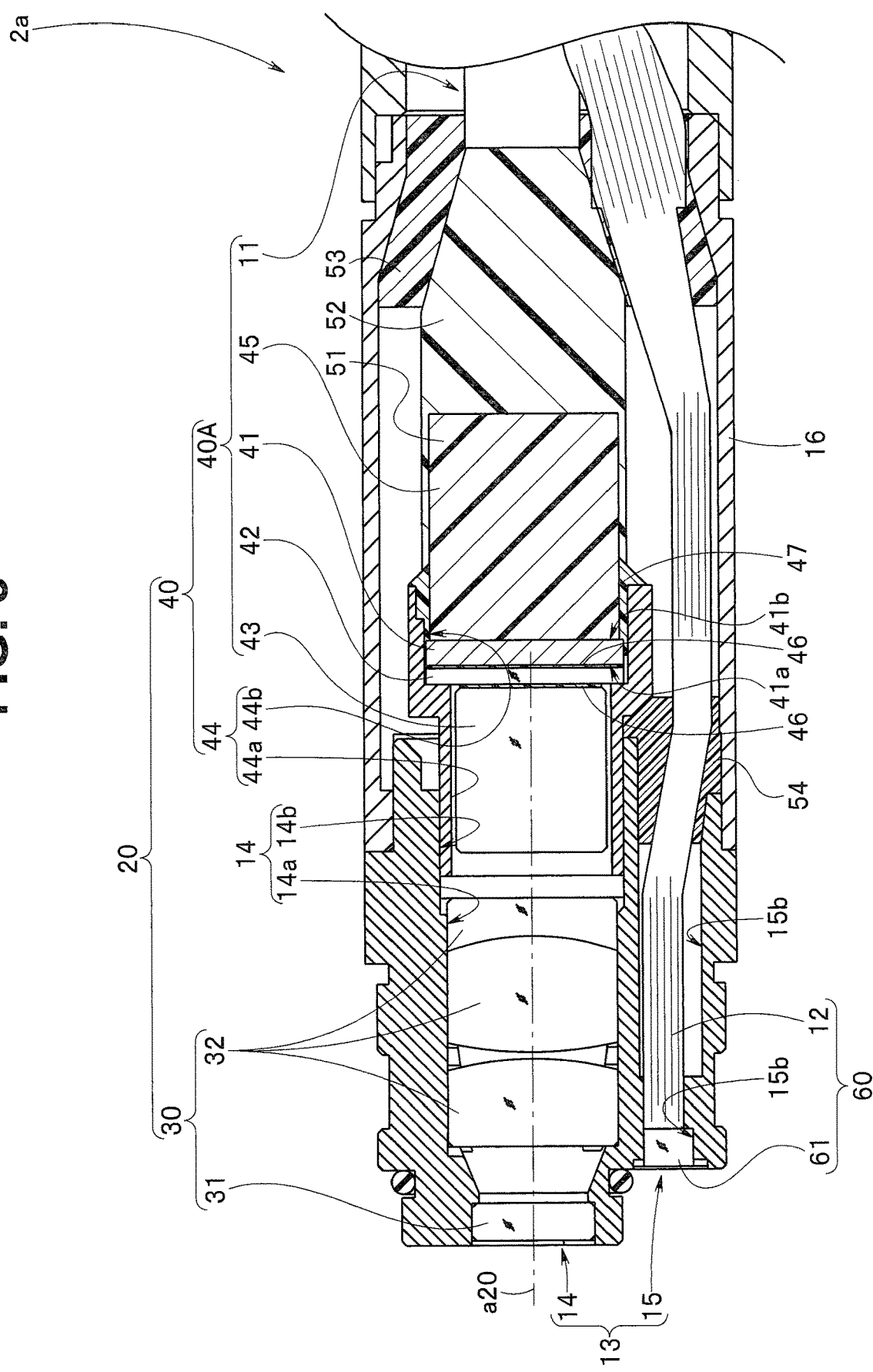
FIG. 3 is a diagram illustrating the observation unit.

As illustrated in FIG. 3, the image pickup unit 20 includes an objective optical unit 30 and a device unit 40.

The objective optical unit 30 mainly includes an observation lens 31, a plurality of optical lenses 32 and an aperture. The observation lens 31, the plurality of optical lenses 32 and the aperture are integrally fixedly provided inside an objective optical unit hole 14a included on the distal end side of the image pickup unit hole 14.

Reference numeral 14b denotes a device frame hole provided on the proximal end side of the image pickup unit hole 14.

The device unit 40 includes an image pickup device 41, a glass lid 42 and a glass cover 43, a device frame 44, and an image pickup circuit portion 45 and the image pickup cable 11. In the present embodiment, the device unit 40 is configured by integration of the device frame 44 and an image pickup section set 40A.

The device frame 44, which is a frame body, includes a distal end-side space denoted by reference numeral 44a and a proximal end-side space denoted by reference numeral 44*b*. The area of a cross-section orthogonal to an optical axis a20 of the proximal end-side space 44*b* is set to be larger than the area of a cross-section orthogonal to an optical axis a20 of the distal end-side space 44*a*.

The image pickup device 41, which is an electronic component, is an area image sensor of, e.g., CCD (charge-coupled device) or CMOS (complementary metal-oxide semiconductor), the area image sensor being configured to output an electric signal corresponding to shot light incident on a light receiving surface.

The glass lid 42 and the glass cover 43 form a device front-side optical member disposed on the front side relative to a device front face 41*a* including the light receiving surface of the image pickup device 41.

The glass lid 42 is disposed on the device front face 41*a* so as to cover the light receiving surface of the image pickup device 41 and is fixed to the device front face 41*a* in an integrated manner by the optical adhesive 46. The glass lid 42 is a device-side optical member disposed on the device side of the device front-side optical member. The glass lid 42 is disposed in a loose fit inside the proximal end-side space 44*b*. The glass lid 42 of the present embodiment is a flat thin plate. The optical adhesive 46 is what is called a UV curable resin.

The glass cover 43 is fixed to a distal end face of the glass lid 42 in an integrated manner by at least one optical adhesive 46 disposed on the distal end face. The glass cover 43 is a distal end-side optical member disposed on the distal end side of the device front-side optical member, the distal end-side optical member being a flat pillar-like shape. The glass lid 42 is disposed in a loose fit inside the distal end-side space 44*a*.

The glass lid 42 and the glass cover 43 integrated with each other project on the distal end side relative to the device front face 41*a* of the image pickup device 41.

The image pickup circuit portion 45 is a device rear-side member provided on the proximal end side opposite to the device front face 41*a* of the image pickup device 41. The image pickup device 41 and the image pickup circuit portion 45 are disposed in a predetermined state inside the proximal end-side space 44*b*.

The image pickup circuit portion 45 includes, for example, two circuit boards 45*a*, 45*b* and two flexible printed boards 45*c*, 45*d* as illustrated in FIG. 4A.

Pins 41*p* of the image pickup device 41 and respective one end sides of the flexible printed boards 45*c*, 45*d* are connected via respective conductive fixing members. Respective other end sides of the flexible printed boards 45*c*, 45*d* are connected to the circuit board 45*a*, 45*b* via respective conductive fixing members. The circuit boards 45*a*, 45*b* are connected via connection terminals 45*e*. Signal wires 11*a* inserted inside the image pickup cable 11 are connected to the connection terminals 45*e* and connection portions of the circuit boards 45*a*, 45*b* via respective conductive fixing members.

A plurality of electronic components (not illustrated) are mounted on the circuit boards 45*a*, 45*b*. A sealing resin is charged between the image pickup device 41 and the first circuit board 45*a*, between the first circuit board 45*a* and the second circuit board 45*b* and around the flexible printed boards 45*c*, 45*d* and the connection terminals 45*e*. In other words, reference numeral 45 in FIG. 3 denotes the image pickup circuit portion 45 covered by a first sealing resin 51.

Reference numeral 52 in FIG. 3 denotes a second sealing resin. The second sealing resin 52 collectively covers and protects contact portions and the plurality of signal wires 11*a* bonded to the contact portions. The second sealing resin 52 covers the periphery of the circuit boards including the contact portions and the distal end side of the image pickup cable 11.

As a result, the image pickup section set 40A is configured. As illustrated in FIG. 4A, the image pickup section set 40A includes the glass cover 43, the glass lid 42, the image pickup device 41 and the image pickup circuit portion 45 in the mentioned order from the distal end side, and the image pickup cable 11 is connected to the circuit portion 45.

Figure 4B:
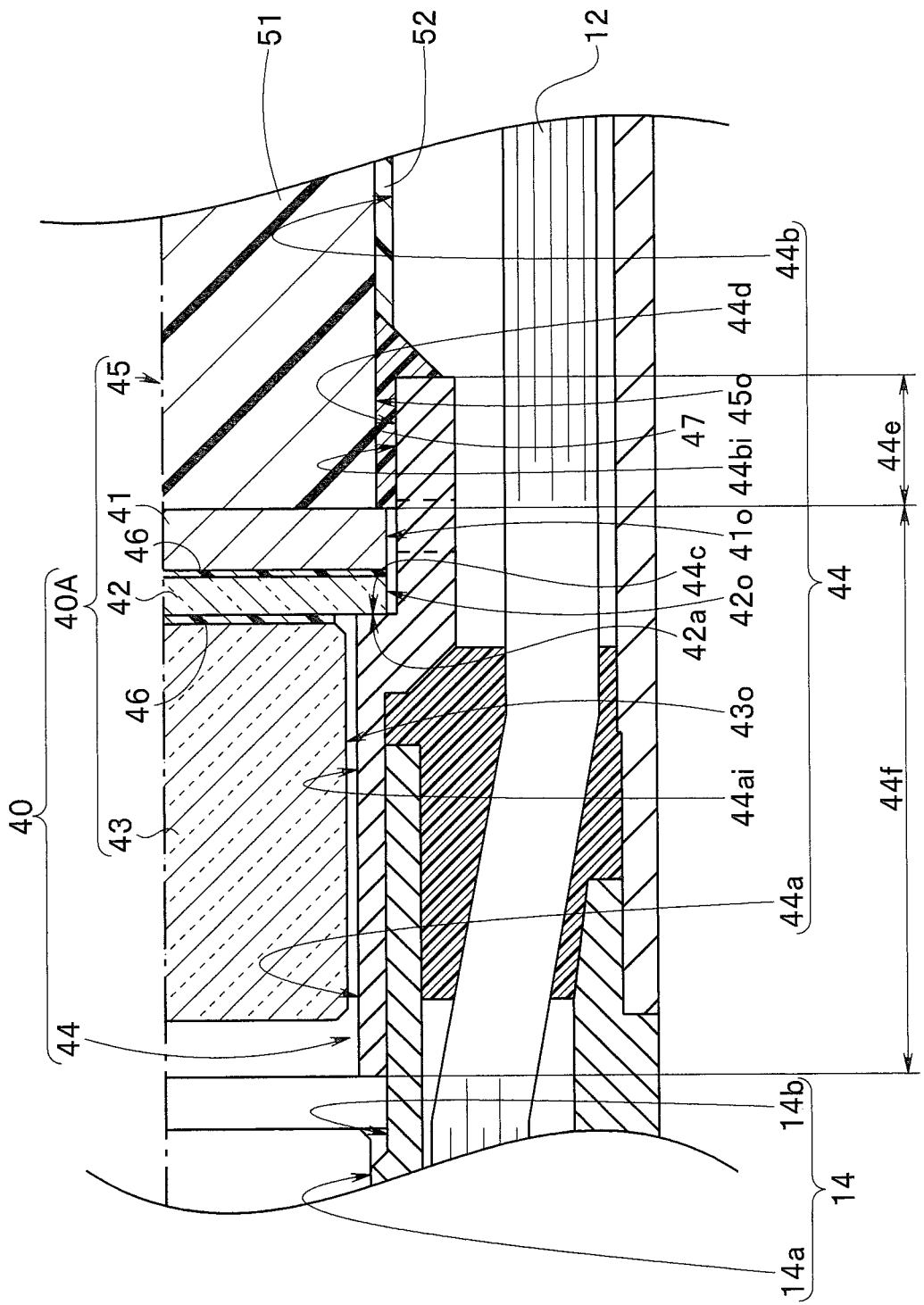
FIG. 4B is a diagram illustrating a device unit.

The device unit 40 will be described with reference to FIG. 4B.

The device unit 40 in the present embodiment is configured by fixing the image pickup circuit portion 45 of the image pickup section set 40A to inner faces of the device frame 44. Reference numeral 47 denotes a fixing member. The fixing member 47 is a first adhesive.

The glass cover 43 of the image pickup section set 40A is disposed inside the distal end-side space 44*a* through the proximal end-side space 44*b* of the device frame 44. In this disposition, a front face 42*a* of the glass lid 42 abuts on an abutment surface 44*c*.

The abutment surface 44*c* is a bottom face of the proximal end-side space 44*b*. The abutment surface 44*c* is a level difference surface between the distal end-side space 44*a* and the proximal end-side space 44*b*.

In this abutment state, the glass cover 43 of the image pickup section set 40A is disposed inside the distal end-side space 44*a*. On the other hand, the glass lid 42, the image pickup device 41 and the image pickup circuit portion 45 are disposed inside the proximal end-side space 44*b*.

Then, outer faces 45*o* of the image pickup circuit portion 45 and the inner faces of the device frame 44 are integrally fixed by the fixing member 47. As a result, the device unit 40 is configured.

The fixing member 47 is an adhesive charged and cured in a gap between the outer faces 45*o* of the image pickup circuit portion 45 and fixing surfaces 44*d* of proximal end-side frame inner faces 44*bi* forming the proximal end-side space 44*b*, the fixing surfaces 44*d* facing the outer faces 45*o*. The outer faces 45*o* and the fixing surfaces 44*d* are fixed by the cured fixing member 47.

In the device unit 40 in which the image pickup circuit portion 45 is fixed to the device frame 44 by the fixing member 47, respective gaps are formed between distal end-side frame inner faces 44*ai* forming the distal end-side space 44*a* of the device frame 44 and outer faces 43*o* of the glass cover 43, between the proximal end-side frame inner faces 44*bi* and outer faces 42*o* of the glass lid 42 and between the proximal end-side frame inner faces 44*bi* and outer faces 41*o* of the solid-state image pickup device 41, forming a non-fixed state in which the glass cover 43, the glass lid 42 and the solid-state image pickup device 41 are not fixed to the device frame 44 in an integrated manner by the fixing member 47.

In other words, in the device frame 44, inner faces of the device frame 44, the inner faces facing the outer faces 43*o* of the glass cover 43, the outer faces 42*o* of the glass lid 42 and the outer faces 41*o* of the solid-state image pickup device 41 are non-fixing surfaces.

The device frame 44 includes an adhesive-charged region 44*e* for charging the fixing member 47 for bonding and fixing and a non-fixing region 44*f*, which is a non-fixing portion with no fixing member 47 for bonding charged. The adhesive-charged region 44*e* is a fixing region of the device frame 44.

The device unit 40 configured as described above is disposed in the device frame hole 14b of the image pickup unit hole 14 and fixed to the device frame hole 14b in an integrated manner after focus adjustment and thus forms the image pickup unit 20. Reference numeral 53 denotes a second adhesive. The second adhesive 53 is a sealing member. The second adhesive 53 is charged inside a metal outer covering frame 16 positioned on the distal end side relative to the bending portion 2b and integrates the image pickup cable 11 and the light guide bundle 12 inserted inside the outer covering frame 16 and the outer covering frame 16 with each other.

The insertion portion 2 including the image pickup unit 20 configured as described above is used for observation under high temperature as stated above. Then, the image pickup device 41, the glass lid 42, the glass cover 43, the device frame 44, the optical adhesive 46, the fixing member 47 and the sealing resins 51, 52 of the image pickup unit 20 expand. The outer faces 42o of the glass lid 42 bonded to the front face 41a of the image pickup device 41 and the outer face 43o of the glass cover 43 are included in the non-fixing portion. Therefore, stress due to the expansion of the fixing member 47 is prevented from being transmitted from the image pickup device 41 directly to the optical adhesive 46 bonding the image pickup device 41 and the glass lid 42, as stress causing detachment of the image pickup device 41 and the glass lid 42 from each other. Accordingly, the trouble of the image pickup device 41 and the glass lid 42 being detached by stress generated by expansion of the fixing member 47 can be prevented.

Also, the insertion portion 2 including the image pickup unit 20 is inserted into a complicatedly flexed conduit. At this time, as stated above, tension occurs in the image pickup cable by the insertion portion 2 being flexed or the bending portion 2b being bent. Tension generated at this time is transmitted to the image pickup circuit portion 45 and then transmitted to the image pickup device 41 via side faces of the image pickup circuit portion 45. Therefore, the stress transmitted to the surface of the bonding between the image pickup device 41 and the glass lid 42 is reduced.

As a result of the above, the optical adhesive 46 applied on the surface of the boundary between the image pickup device 41 and the glass lid 42 is prevented from being easily detached, enabling enhancement in durability of the image pickup unit 20.

The illumination unit 60 includes the illumination lens 61 and the light guide bundle 12. The illumination lens 61 is disposed inside a lens hole 15a configuring the distal end side of the illumination hole 15 provided in the distal-end frame member 13 and fixed, for example, by an optical adhesive.

On the other hand, the light guide bundle 12 extends through the inside of a bundle hole 15b configuring the proximal end side of the illumination hole 15. The light guide bundle 12 is fixedly provided inside the bundle hole 15b via a third adhesive 54 charged inside the bundle hole 15b.

A device frame 44A will be described with reference to FIGS. 5A and 5B.

Figure 5A:
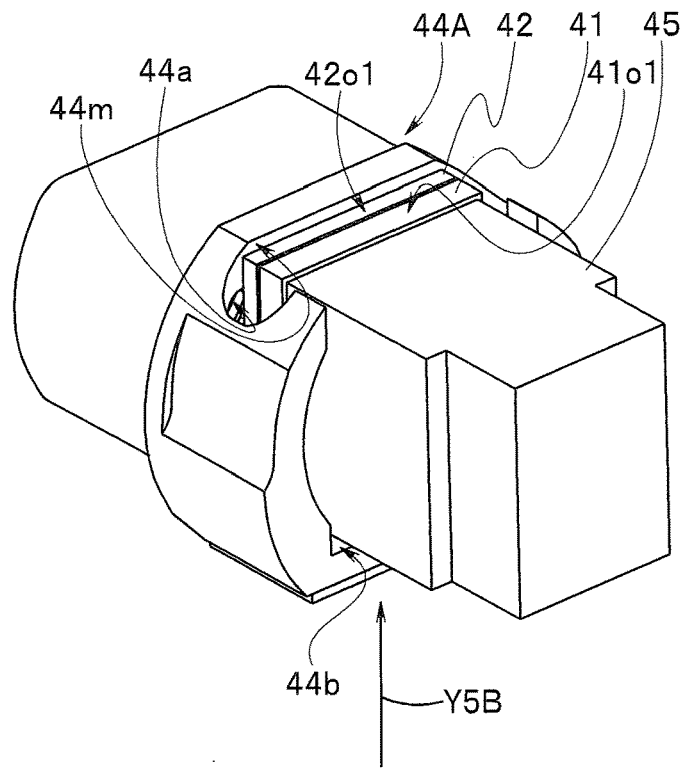
FIG. 5A is a diagram illustrating a configuration of a device frame including a through hole portion and is a diagram illustrating an example configuration including a cutout groove as the through hole portion.
Figure 5B:
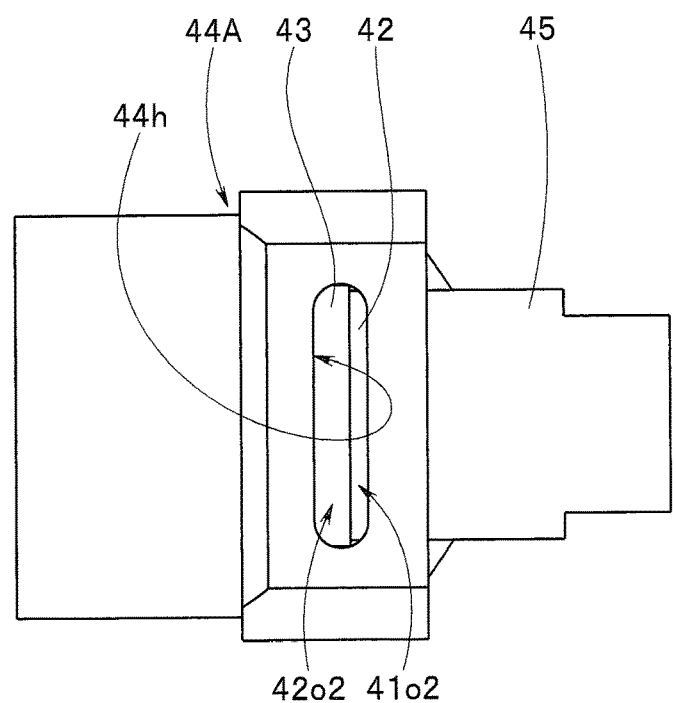
FIG. 5B is a diagram illustrating an example configuration including an opening as the through hole portion.

In the device frame 44A in the present embodiment, a cutout groove 44m, which is illustrated in FIG. 5A, and an opening 44h, which is illustrated in FIG. 5B, are provided as through hole portions that communicate with the outside and spaces 44a, 44b of the device frame 44A in the non-fixing surfaces.

The cutout groove 44m is a groove that makes one surface 42o1 of outer faces 42o of a glass lid 42 and one surface 41o1 of outer faces 41o of an image pickup device 41 be exposed to the outside. On the other hand, the opening 44h is a through hole that makes another surface 42o2 of the outer faces 42o of the glass lid 42 and another surface 41o2 of the outer faces 41o of the image pickup device 41 be exposed to the outside. In the present embodiment, the opening 44h is a long hole in which a plurality of round through holes are aligned, but may be, e.g., a slit.

The other surface 42o2 of the glass lid 42 is a surface on the opposite side of the one surface 42o1 of the glass lid 42. The other surface 41o2 of the image pickup device 41 is a surface on the opposite side of the one surface 41o1 of the image pickup device 41.

Figure 5C:
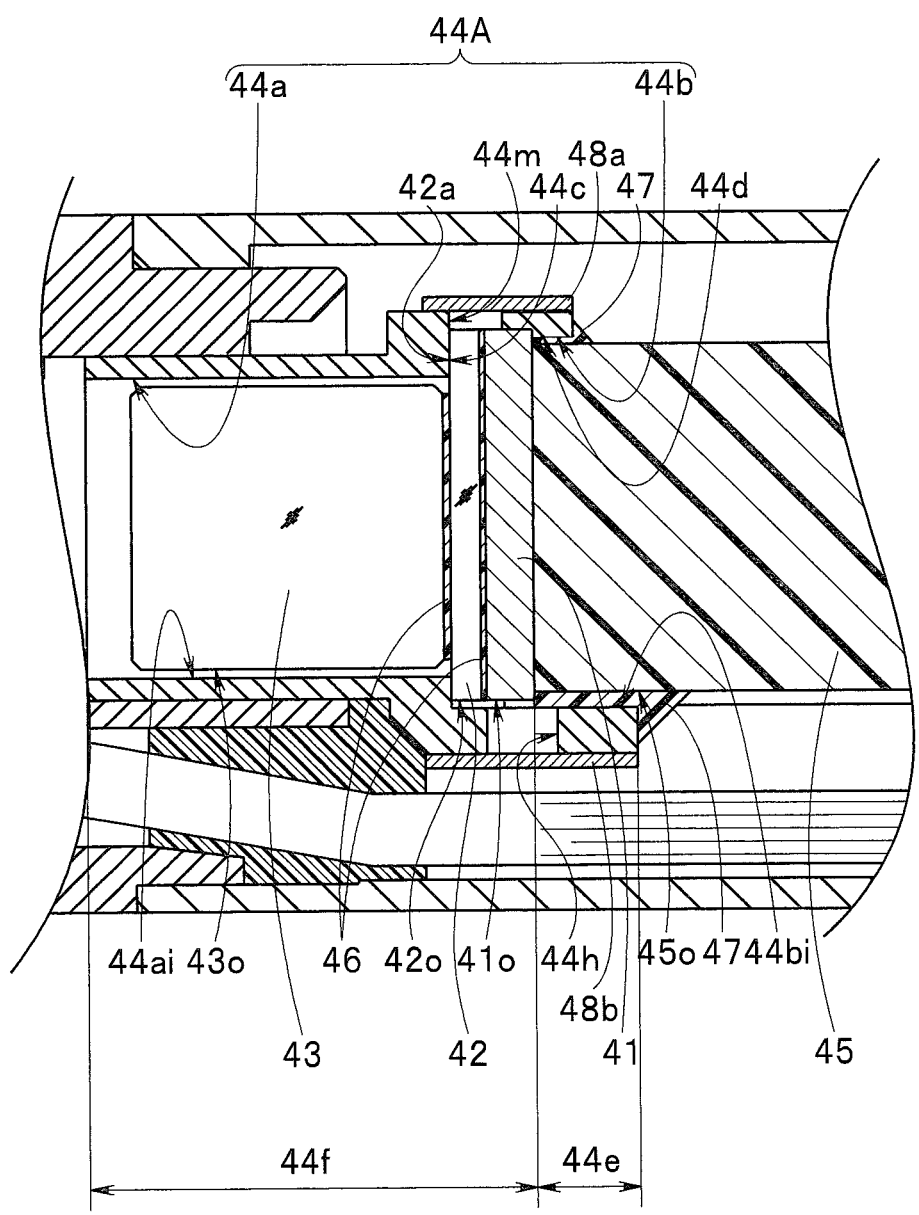
FIG. 5C is a diagram illustrating operation and effects of the through hole portion.

As illustrated in FIG. 5C, an image pickup circuit portion 45 and the device frame 44A are integrally fixed by a fixing member 47. At this time, the fixing member 47 is charged into a gap between outer faces 45o of the image pickup circuit portion 45 and proximal end-side frame inner faces 44bi.

In the present embodiment, in the device frame 44A, the cutout groove 44m and the opening 44h are provided in a positional relationship in which the cutout groove 44m and the opening 44h face each other. Therefore, when an assembly worker charges the fixing member 47 into the gap between the outer faces 45o of the image pickup circuit portion 45 and the proximal end-side frame inner faces 44bi, the worker can quickly perform the charging work while visually confirming a state of application of the fixing member 47.

Therefore, it is possible to solve the trouble of the fixing member 47 adhering to the image pickup device 41 and/or the glass lid 42 and the trouble of the fixing member 47 adhering to the surface of the boundary between the glass lid 42 and the image pickup device 41 while enhancing the assemblability.

According to this configuration, as described above, when tension is generated in the image pickup cable by the insertion portion 2 being flexed or the bending portion 2b being bent, stress is transmitted to the image pickup device 41 only via side surfaces of the image pickup circuit portion 45, the side surfaces including neither the cutout groove 44m nor the opening 44h. In other words, the stress transmitted to the image pickup device 41 is substantially reduced and stress imposed in a direction in which the image pickup device 41 and the glass lid 42 are detached from each other is thus reduced, enabling enhancement in durability of an image pickup unit 20.

Here, reference numerals 48a, 48b in FIG. 5C each denote an occlusion member. Each of the occlusion members 48a, 48b is, for example, a tape and preferably has a light blocking property.

The first occlusion member 48a occludes the cutout groove 44m to prevent foreign substances from entering the inside from the cutout groove 44m. The second occlusion member 48b occludes the opening 44h to block light leaking from a light guide bundle 12 while preventing foreign substances from entering the inside from the opening 44h.

The rest of the configuration is similar to the configuration of the above-described embodiment and members that are the same as the members of the above-described embodiment are provided with reference numerals that are the same as the reference numerals of the members of the above-described embodiment and description of the members are omitted.

In the above-described embodiment, a gap is formed between the distal end-side frame inner faces 44ai forming the distal end-side space 44a of the device frame 44 and the outer faces 43o of the glass cover 43, and the gap serves as a non-fixing portion in which no fixing member 47 is applied, providing a non-fixed state.

Figure 6A:
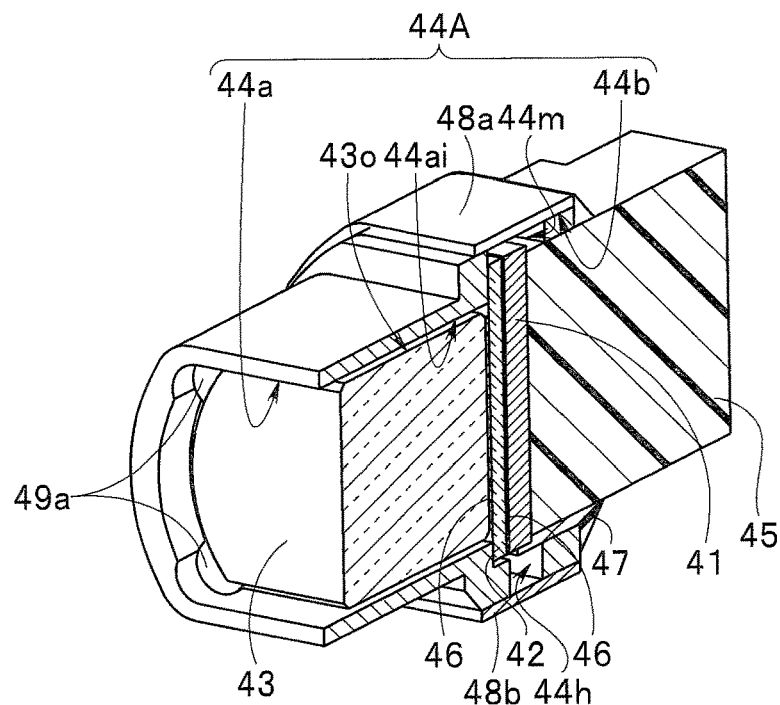
FIG. 6A is a diagram illustrating a configuration in which a glass cover is held by a glass cover holding portion.

However, as illustrated in FIG. 6A, a glass cover holding portion 49a is provided at, for example, four corners on the distal end face side of the device frame 44A in which a glass cover 43 is arranged, in the gap between the distal end-side frame inner faces 44ai of the device frame 44A and outer faces 43o of a glass cover 43. The glass cover holding portions 49a are provided by charging an elastic adhesive from the distal-end opening side of the distal end-side space 44a of the device frame 44A.

The elastic adhesive, when cured, has an elasticity modulus higher than an elasticity modulus of the frame body, and holds the glass cover 43 inside the distal end-side space 44a in such a manner that the glass cover 43 is movable.

According to this configuration, when an impact is given to the image pickup unit 20, a rotational moment generated in the glass cover 43 is absorbed by the glass cover holding portions 49a formed by the elastic adhesive, enabling reduction of the rotational movement imposed on the glass cover 43.

As a result, an impact resistance of the image pickup unit 20 is enhanced and thus damage of the glass cover 43 and detachment of the image pickup device 41 and the glass lid 42 from each other due to an impact are prevented.

Figure 6B:
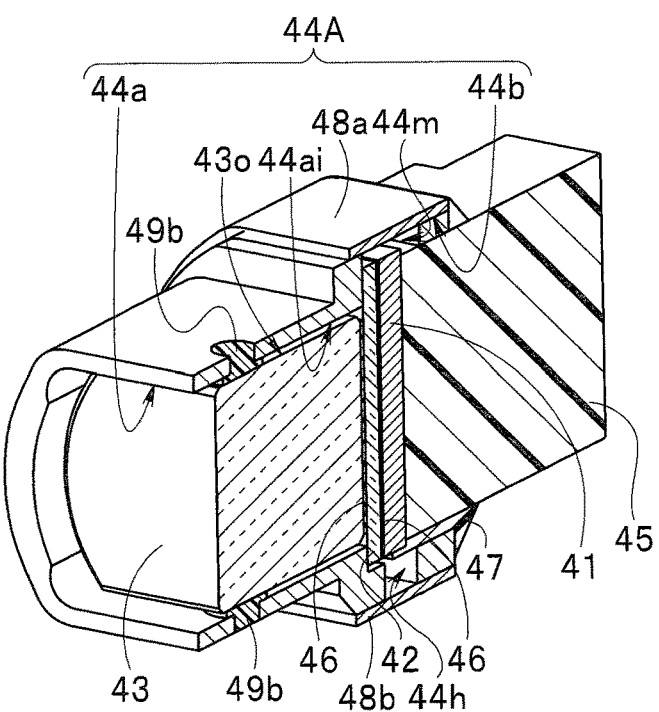
FIG. 6B is a diagram illustrating another configuration in which a glass cover is held by a glass cover holding portion.

Instead of the glass cover holding portions 49a being provided by charging an elastic adhesive from the distal-end opening side of the distal end-side space 44a of the device frame 44A, as illustrated in FIG. 6B, a glass cover holding portion 49b may be provided at each of a plurality of positions. Each of the glass cover holding portions 49b is provided in a gap between a relevant distal end-side frame inner face 44ai and a relevant outer face 43o of a glass cover 43 by providing a through hole 44h that communicates with the outside and the distal end-side frame inner face 44ai side at the predetermined position in the device frame 44A and charging an elastic adhesive into the through hole 44h.

As described above, the glass cover holding portions 49b prevent damage of the glass cover 43 and detachment of the image pickup device 41 and the glass lid 42 from each other due to an impact given to the image pickup unit 20 and thus enable enhancement in durability of the image pickup unit 20.

Also, as a result of the provision of the glass cover holding portions 49a, 49b illustrated in FIG. 6A or 6B, the gap between the distal end-side frame inner faces 44ai and the outer faces 43o of the glass cover 43 becomes an adhesive charged region. However, since the adhesive is an elastic adhesive, the glass cover 43 disposed in the adhesive-charged region is in a non-fixed state.

Also, in the above-described embodiment, a linear expansion coefficient A of the fixing member 47, which is the first adhesive, is set to be equal to or exceed a linear expansion coefficient B of the second adhesive 53. In addition, the linear expansion coefficient A of the fixing member 47 is set to be equal to or exceed a linear expansion coefficient C of the third adhesive 54.

As a result of the above, stress generated by expansion of the second adhesive 53 or expansion of the third adhesive 54 can be prevented from being transmitted directly to the optical adhesive 46 bonding the image pickup device 41 and the glass lid 42 to each other from the image pickup device 41.

Figure 7:
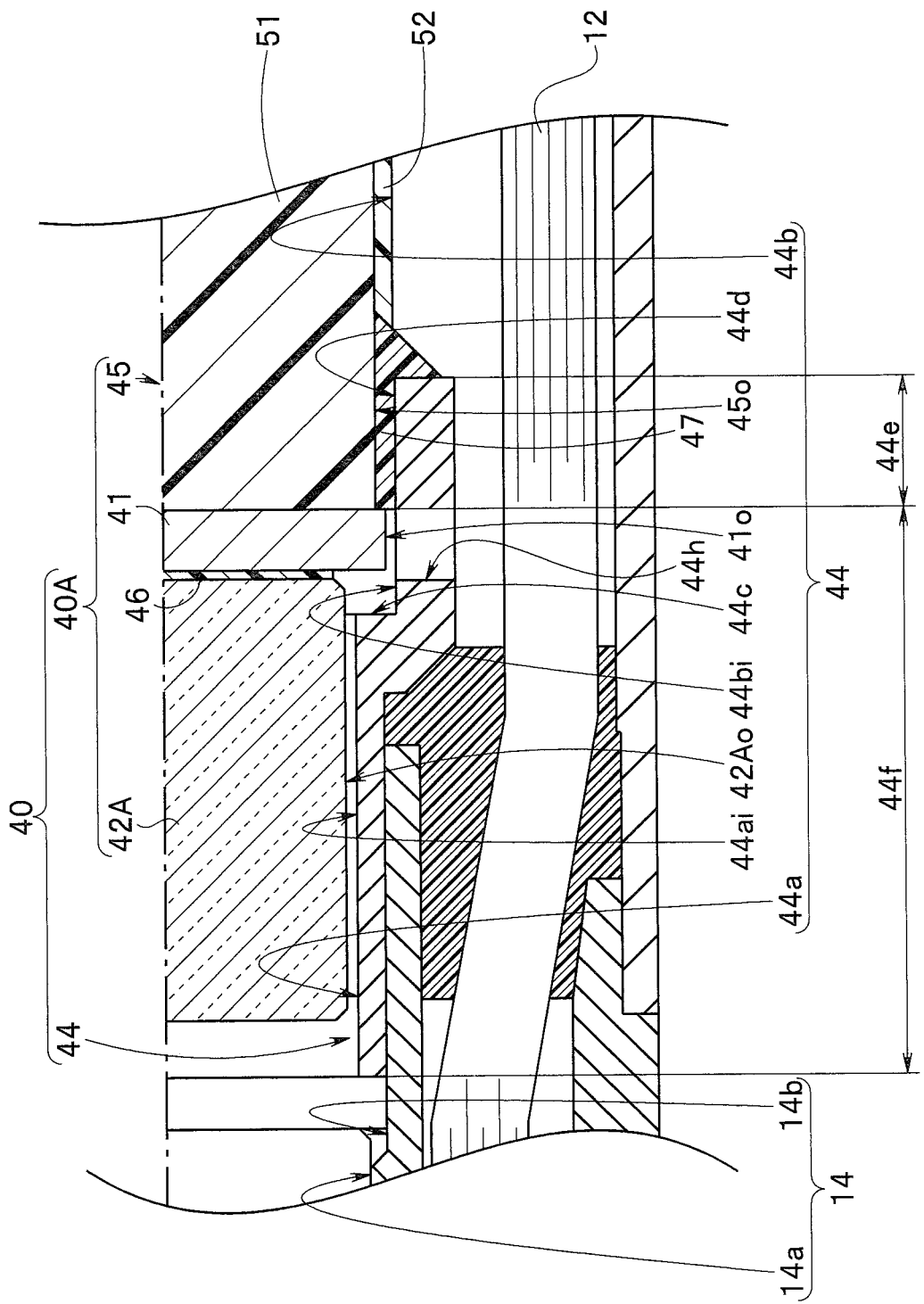
FIG. 7 is a diagram illustrating a device unit including a pillar-like glass lid.

Also, in the above-described embodiment, the device front-side optical member includes the flat plate-like glass lid 42 disposed on the device side and the pillar-like glass cover 43 disposed on the distal end side. However, as illustrated in FIG. 7, the device front-side optical member may be a pillar-like glass lid 42A.

According to this configuration, gaps are formed between distal end-side frame inner faces 44ai forming a distal end-side space 44a of a device frame 44 and outer faces 42Ao of the glass lid 42A, between proximal end-side frame inner faces 44bi and the outer faces 42Ao of the glass lid 42A and between the proximal end-side frame inner faces 44bi and outer faces 41o of a solid-state image pickup device 41, providing a non-fixing portion in which the glass lid 42A and the solid-state image pickup device 41 are not fixed to the device frame 44 in an integrated manner by a fixing member 47.

In the present embodiment, the glass lid 42A includes no surface that abuts on an abutment surface 44c. The rest of the configuration and operation and effects are similar to the configuration and the operation and the effects of the above-described embodiment, and members that are the same as the members of the above-described embodiment are provided with reference numerals that are the same as the reference numerals of the members of the above-described embodiment and description of the members are omitted. Also, in the present embodiment, as described above, the impact resistance of the image pickup unit 20 can be enhanced by providing glass cover holding portions 49a, 49b to the glass lid 42A.

Figure 8A:
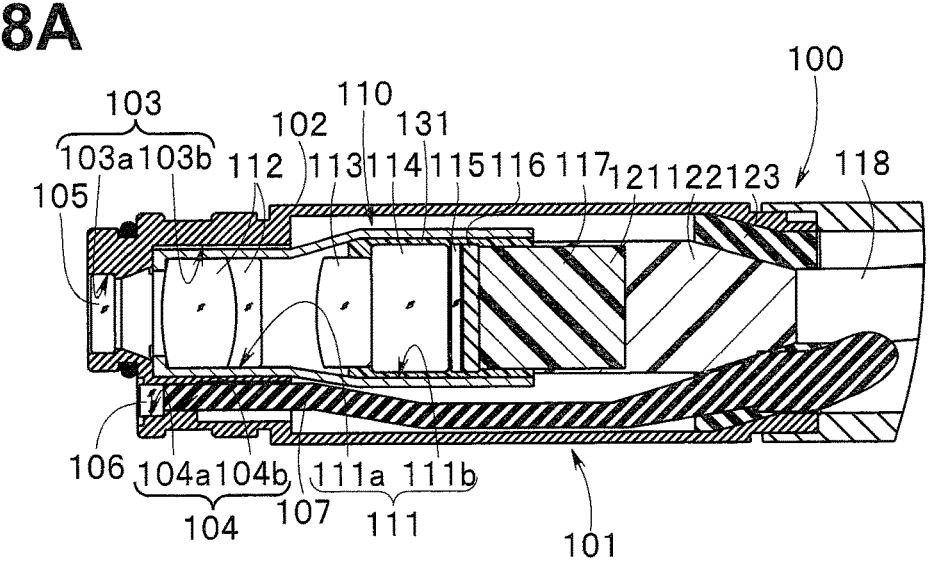
FIG. 8A is a diagram illustrating an example configuration of an image pickup unit in which stress generated by expansion of a fixing portion becomes stress imposed on a bonding part of bonding between a glass lid and an image pickup device in a direction in which the glass lid and the image pickup device are detached from each other.

An insertion portion to which an optical adapter is removably attachable can be configured as illustrated in FIG. 8A.

As illustrated in FIG. 8A, a distal end portion 101 of an insertion portion 100 includes a distal-end rigid frame 102. An image pickup unit hole 103 and an illumination hole 104 are provided in the distal-end rigid frame 102.

The image pickup unit hole 103 includes a lens hole 103a and a unit hole 103b. An observation lens 105 is fixedly provided in the lens hole 103a and an image pickup unit 110 is arranged in the unit hole 103b.

The illumination hole 104 includes a lens hole 104a and a bundle hole 104b. An illumination lens 106 is fixedly provided in the lens hole 104a and a light guide bundle 107 is arranged in the bundle hole 104b.

The image pickup unit 110 includes one or more distal end-side lenses 112 and an intermediate lens 113, a glass cover 114, a glass lid 115, an image pickup device 116 and an image pickup circuit portion 117 arranged inside a unit frame 111 including a distal end-side space portion 111a and a proximal end-side space portion 111b. The intermediate lens 113, the glass cover 114, the glass lid 115 and the image pickup device 116 are integrated via, for example, an optical adhesive.

Then, the intermediate lens 113, the glass cover 114, the glass lid 115, the image pickup device 116 and the image pickup circuit portion 117 are integrally fixed by providing a first fixing portion 131 at a predetermined position in inner faces of the unit frame 111. Here, the first fixing portion 131 is applied with the adhesive to be cured between the inner faces of the unit frame 111, and outer faces of the intermediate lens 113, outer faces of the glass cover 114, outer faces of the glass lid 115, outer faces of the image pickup device 116 and outer faces of the image pickup circuit portion 117.

Reference numeral 118 denotes an image pickup cable extending from the proximal end side of the image pickup circuit portion 117. The image pickup circuit portion 117 is covered by a first sealing resin 121, and the periphery of contact portions of the image pickup circuit portion 117 and a plurality of signal wires bonded to the contact portions is covered by a second sealing resin 122.

The image pickup unit 110 is disposed inside the unit hole 103b and is fixed by means of, for example, bonding. Also, the image pickup cable 118 and the light guide bundle 107 extending from the inside of the distal-end rigid frame 102 are integrated with the proximal end side of the rigid frame 102 via a third sealing resin 123 to configure the insertion portion 100.

When the insertion portion 100 configured as described above is used for observation under high temperature, the unit frame 111, the intermediate lens 113, the glass cover 114, the glass lid 115, the image pickup device 116, the image pickup circuit portion 117, the first fixing portion 131 and the sealing resins 121, 122, 123 in the image pickup unit 110 expand.

At this time, stress generated by expansion of the first fixing portion 131 may be imposed on the part of bonding between the glass lid 115 and the image pickup device 116 as stress in a direction in which the glass lid 115 and the image pickup device 116 are detached from each other.

Then, as a result of the stress acting as stress in the direction in which the glass lid 115 and the image pickup device 116 are detached from each other, the glass lid 115 and the image pickup device 116 are detached from each other, which causes an image defect.

In order to prevent the detachment of the glass lid 115 and the image pickup device 116 from each other, it is necessary to prevent stress from being imposed in the direction of the detachment. For that purpose, it is conceivable that a second fixing portion 132 is provided as illustrated in FIG. 8B or a third fixing portion 133 is provided as illustrated in FIG. 8C.

The fixing portions 131, 132, 133 are configured by applying, for example, a same adhesive, which is a fixing member.

Figure 8B:
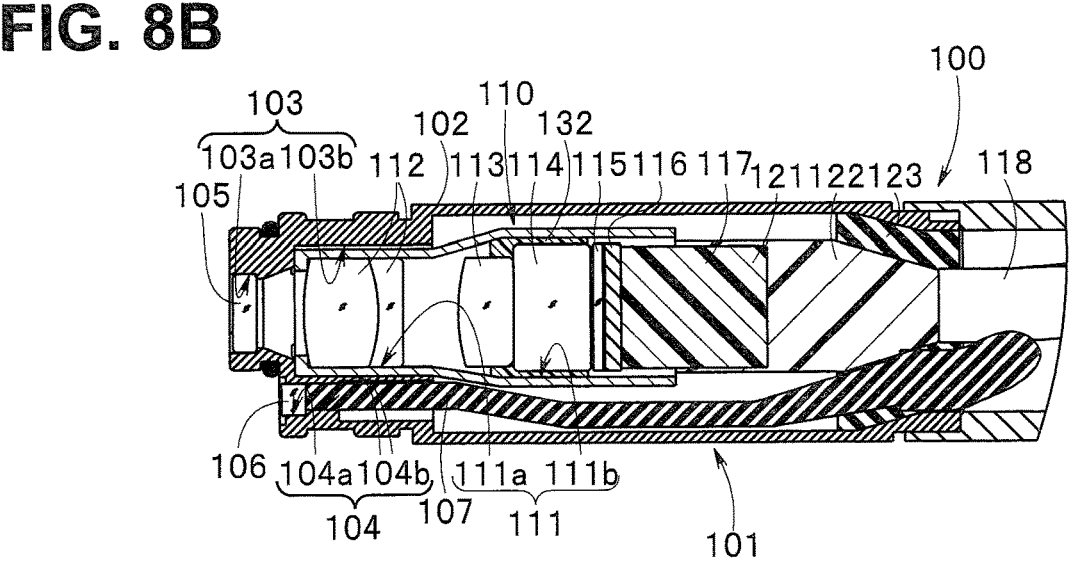
FIG. 8B is a diagram illustrating an example configuration of an image pickup unit that is a modification of the image pickup unit in FIG. 8A, in which stress generated by expansion is less likely to become stress imposed on a bonding part of bonding between a glass lid and an image pickup device in a direction in which the glass lid and the image pickup device are detached from each other but tension generated in an image pickup cable becomes stress imposed on the bonding part in the direction of the detachment.
Figure 8C:
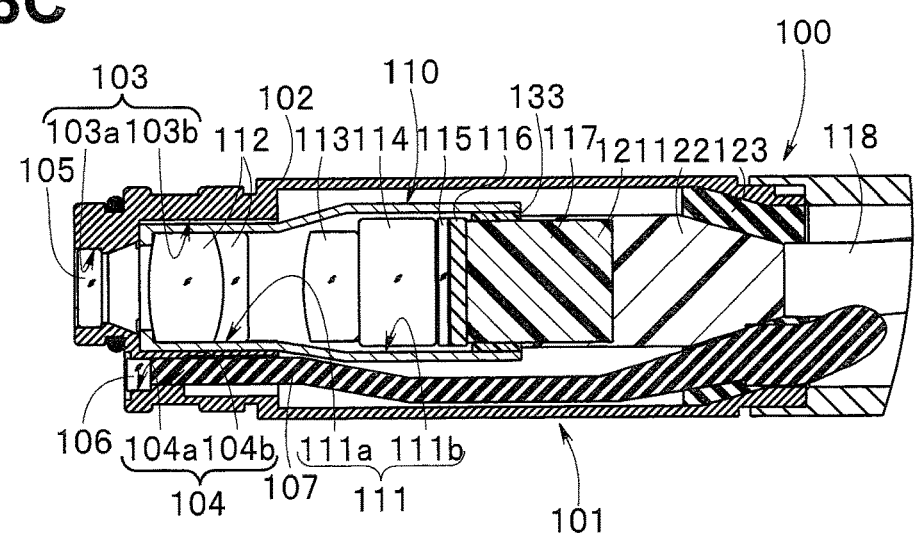
FIG. 8C is a diagram illustrating an example configuration of an image pickup unit that is another modification of the image pickup unit in FIG. 8A, in which stress generated by expansion and tension generated in an image pickup cable are less likely to become stress imposed on a bonding part of bonding between a glass lid and an image pickup device in a direction in which the glass lid and the image pickup device are detached from each other.

In FIG. 8B, the second fixing portion 132 is applied with the adhesive to be cured between inner faces of a unit frame 111, and outer faces of an intermediate lens 113 and outer faces of the glass cover 114. As a result, the intermediate lens 113 and the glass cover 114 are fixed to the unit frame 111 by the second fixing portion 132.

In this configuration, the intermediate lens 113 and the glass cover 114 of an image pickup unit 110 are fixed to the unit frame 111 by providing the second fixing portion 132, and an image pickup circuit portion 117, an image pickup device 116 and a glass lid 115 bonded to a front face of the image pickup device 116 are not fixed to the unit frame 111.

Therefore, in observation under high temperature, stress generated by expansion of the second fixing portion 132 is prevented from being directly transmitted as stress causing detachment of the image pickup device 116 and the glass lid 115 from each other, and thus, the trouble of detachment of the image pickup device 116 and the glass lid 115 from each other by stress caused by expansion of the second fixing portion 132 can be prevented.

However, in this configuration, as described above, when tension is generated in an image pickup cable, the tension is directly applied to the part of the bonding between the image pickup device 116 and the glass lid 115 and thus stress in a direction in which the image pickup device 116 and the glass lid 115 are detached from each other is imposed on the bonding part.

In other words, in a structure in which the intermediate lens 113 and the glass cover 114 are fixed to the unit frame 111 by provision of the second fixing portion 132, the trouble of stress causing detachment of the image pickup device 116 and the glass lid 115 from each other being imposed by expansion of the second fixing portion 132 can be prevented.

However, when tension occurs in the image pickup cable, the tension acts as stress in the direction in which the image pickup device 116 and the glass lid 115 are detached from each other. As a result, the glass lid 115 and the image pickup device 116 are detached from each other by the stress generated by the tension, which causes an image defect.

In FIG. 8C, a third fixing portion 133 is applied with the adhesive to be cured between inner faces of a unit frame 111 and outer faces of an image pickup circuit portion 117. As a result, only the image pickup circuit portion 117 is fixed to the unit frame 111 by provision of the third fixing portion 133.

In this configuration, the image pickup circuit portion 117 of an image pickup unit 110 is fixed by provision of the third fixing portion 133 and an intermediate lens 113, a glass cover 114, a glass lid 115 and an image pickup device 116 are not fixed to the unit frame 111.

Therefore, in observation under high temperature, stress generated by expansion of the third fixing portion 133 is prevented from being directly transmitted as stress causing detachment of the image pickup device 116 and the glass lid 115 from each other, and thus, the trouble of detachment of the image pickup device 116 and the glass lid 115 from each other by stress generated by expansion of the third fixing portion 133 can be prevented.

On the other hand, when tension is generated in an image pickup cable, as with the above-described image pickup unit 20 in FIG. 3, tension generated in the image pickup cable 118 is transmitted to the image pickup circuit portion 117 and then transmitted to the image pickup device 116 via side faces of the image pickup circuit portion 117. Therefore, stress transmitted to the part of bonding between the image pickup device 116 and the glass lid 115 is reduced.

In other words, the trouble of detachment of the glass lid 115 and the image pickup device 116 from each other by stress generated by expansion of the third fixing portion 133 or tension can be reduced.

In other words, instead of the image pickup unit 110 provided with the first fixing portion 131 illustrated in FIG. 8A being formed, as with the above-described image pickup section set 40A in the image pickup unit 20, the image pickup unit 110 provided with the third fixing portion 133 illustrated in FIG. 8C is formed to provide a non-fixing portion in which the glass cover 114, the glass lid 115 and the image pickup device 116 are not fixed to the unit frame 111. As a result, reduction of the trouble of detachment of the glass lid 115 and the image pickup device 116 from each other is enabled.

The present invention is not limited only to the above-described embodiment but various modifications are possible without departing from the spirit of the invention.

What is claimed is:

1. An endoscope apparatus comprising:
   an image sensor;
   a device front-side optical member provided on a distal end side ahead of a light receiving surface of the image sensor, the device front-side optical member being fixed to a front face of the image sensor in an integrated manner;
   a frame that covers at least a part of the image sensor and covers at least a part of the device front-side optical member;
   a circuit board provided on a proximal end side of the image sensor, the proximal end side being opposite to the front face of the image sensor; and an adhesive for fixing the circuit board to the frame;
wherein a gap is formed between the frame and a side surface of the image sensor and between the frame and a side surface of the device front-side optical member; and
the gap does not include a fixing member disposed therein such that the frame and the side surface of the device front-side optical member are not directly fixed to each other.

2. The endoscope apparatus according to claim 1, wherein:
the device front-side optical member includes a device-side optical member adhered and fixed to a distal end side of the light receiving surface of the image sensor, and a distal end-side optical member adhered and fixed to a distal end side of the device-side optical member; and
a side surface of the device-side optical member and a side surface of the distal end-side optical member are covered by the frame and the gap is formed between the side surfaces and the frame.

3. The endoscope apparatus according to claim 1, wherein the frame includes an abutment surface which abuts a part of a front face of a device-side optical member of the device-front side optical member fixed to the light receiving surface of the image sensor.

4. The endoscope apparatus according to claim 1, wherein the frame includes a through hole that allows an outside and the gap to communicate with each other.

5. The endoscope apparatus according to claim 4, wherein the through hole included in the frame body is occluded by an occlusion member.

6. The endoscope apparatus according to claim 1, wherein:
the gap is a first gap;
the device front-side optical member includes a distal end-side optical member fixed to a distal end face of a device-side optical member;
the distal end-side optical member is covered by the frame, a second gap, different from the first gap, is formed between a side surface of the distal end-side optical member and the frame, and at least a part of the second gap is provided with a fixing member having an elasticity modulus that is higher than an elasticity modulus of the frame, and
the distal end-side optical member is held in the frame by the fixing member such that the distal end-side optical member is movable relative to the frame.

7. The endoscope apparatus according to claim 1:
wherein the adhesive is a first adhesive that fixes the frame to the circuit board;
the endoscope apparatus further comprising:
a second adhesive that integrally fixes an image pickup cable and a light guide to a metal frame surrounding the image pickup cable and the light guide on a distal end side of a bending portion; and
a third adhesive that is charged into a hole in which the light guide of an illumination unit disposed adjacent to an image pickup unit is inserted and holds the light guide,
wherein a relationship of $A \geq B$ and $A \geq C$ is set among a linear expansion coefficient A of the first adhesive, a linear expansion coefficient B of the second adhesive and a linear expansion coefficient C of the third adhesive.

8. The endoscope apparatus according to claim 1, wherein the device front-side optical member is a glass lid that covers the light receiving surface of the image sensor, the glass lid being fixed to the front face of the image sensor by an optical adhesive.

9. The endoscope apparatus according to claim 1, wherein the adhesive is an optical adhesive.

10. The endoscope apparatus according to claim 6, wherein the fixing member is an elastic adhesive.

* * * * *